United States Patent [19]

Baumberg

[11] Patent Number: 4,538,619

[45] Date of Patent: Sep. 3, 1985

[54] ANALYZER OF IMPULSE PROCESSES OF HEART ACTIVITY

[76] Inventor: Iosif Baumberg, 54 Bay 29 St., #5B, Brooklyn, N.Y. 11214

[21] Appl. No.: 549,889

[22] Filed: Nov. 9, 1983

[51] Int. Cl.³ .............................................. A61N 5/04
[52] U.S. Cl. .................................................. 128/702
[58] Field of Search ................................ 128/695–698, 128/702–708

[56] References Cited

U.S. PATENT DOCUMENTS

| | | | |
|---|---|---|---|
| 3,552,586 | 1/1971 | Horth | 128/703 |
| 3,586,835 | 6/1971 | Foeh, Jr. | 128/706 |
| 3,773,038 | 11/1973 | Smith et al. | 128/706 |
| 3,837,333 | 9/1974 | Bruckheim | 128/706 |
| 3,952,731 | 4/1976 | Worstencroft | 128/702 |
| 4,221,223 | 9/1980 | Linden | 128/706 |

*Primary Examiner*—William E. Kamm
*Attorney, Agent, or Firm*—Ilya Zborovsky

[57] ABSTRACT

An analyzer of impulse processes of heart activity has increased functional possibilities with a portable construction and determines an index of arrhythmia, a total value of arrhythmia and a relative value of arrhythmia.

4 Claims, 6 Drawing Figures

ANALYZER OF IMPULSE PROCESSES OF HEART ACTIVITY

BACKGROUND OF THE INVENTION

The present invention relates generally to an analyser of impulse processes of heart activity which is element of medical equipment which will find its application as a device for individual use, in the self-control of conditions of heart activity.

Depending upon the task of the control, in accordance with the physician's prescription, the detectors of impulse processes of heart activity are used for example, for detecting pulse, heart beats or bioelectric potentials. Many types of portable devices for individual use which have various constructions are known, such as pulse meters operating to determine an average frequency $F_e$ of respective pulse beats, which is defined by the number of pulse beats per time unit, such as for example per minute.

The disadvantages of known pulse meters are their limited functional possibilities, since they are designed to determine only one parameter of the process to be analysed, namely the average frequency of impulses. Another disadvantage of the known pulse meters is their susceptibility to disturbances which can significantly influence the reading.

SUMMARY OF THE INVENTION

Accordingly, it is an object of the present invention to avoid the afore-mentioned disadvantages.

In particular, the object of the invention is to provide an improved analyser of impulse processes of heart activity which has increased functional possibilities of portable device.

Another object of this invention is to provide a portable device suitable for individual use, which in addition to the determination of average frequency $F_e$ of heart beats, is capable of determining values of the following parameters:

1. Index of arrhythmia or in other words, the frequency of occurances (i.e. percentage of the total number of time intervals to be compared) of unequal values of time intervals between the immediately following impulses of the impulse sequence under test, the frequency being determined either from the set of all time intervals between the impulses of the impulse sequence under test or from a representative sample of such intervals;

2. Total value of arrhythmia determined as a sum of absolute values of differences between the values of time intervals between the immediately following impulses of the impulse flow to be analyzed, both in the total amount and in a selective sample amount of time intervals expressed in time units;

3. Relative value of arrhythmia which is an average value of differences of unequal time intervals between the impulses of the inpulse sequence to be analyzed.

A further object of the invention is also to reduce the influence of accidental errors upon the process of detecting the impulses of heart activity such as, for example impulses of heart beat.

In keeping with these objects and others which will become apparent hereinafter, one feature of the invention resides in an analyzer of impulse processes of heart activity of the aforementioned type, in the combination of the following features:

1. A source of input pulses detected by a suitable detector of conventional design is connected through a first input of a first logic element (gate) AND and to the input of a counter of impulses having a plurality R of outputs. One of the outputs of the counter of impulses (output $M \geq 1$) is connected with the aid of an R-position switch SW for selecting the range of measurements in dependency on the required range ($M = 1,2 \ldots R$) and via an inverter 2 to the other input of the first AND gate, with the inlet of a signalling device, such as for example a sound or optical indicator (ALARM), and with a first input of an OR gate; the output of the first AND gate is connected with the input of a counting trigger circuit FF (a flip-flop with a counting input) and with the R input of an an RS-flip-flop. The Q output of the RS-flip-flop is connected with the second input of the OR gate; the output of the OR gate is connected via an inverter 2 to an inlet of a second AND gate, the other input of which being connected to a clock pulse generator; the output of the second AND gate is connected with the inlet of a first reading counter of impulses provided with a digital indicator (COUNT 1); and being further connected with second inputs of third and fourth AND gates; the Q output of the counting trigger is connected to the first input of the third AND gate, the inverse output $\overline{Q}$ of the trigger circuit is connected with the inlet of a multivibrator MV (impulse former) and with the first input of the fourth AND gate. The output of the fourth AND gate is connected with the summarizing or upward counting input of an up-down counter of impulses. The downward counting input of the later counter is connected with the output of the third AND gate and with a first input of a fifth AND gate; the second input of the fifth AND gate is connected with the output of a NOR gate having a plurality of inputs K each connected to a corresponding K output of the up-down counter. The nulifying or clear (CL) input of the up-down counter is connected with the output of the multivibrator MW and with the S input of a second RS-flip-flop. The rest (R) input of the second RS-flip-flop is connected to the output of the fifth AND gate and with the inlet of a second reading counter of impulses provided with the digital count indicator; the $\overline{Q}$-output of the second RS-flip-flop is connected with the inlet of a third reading counter of impulses provided with the digital count indicator.

2. In a modification, the aforedescribed analyzer of the impulse processes of heart activity is characterized in that, for the purpose of decreasing the influence of the periodicity of the impulse processes to be analysed upon the results of measurements, and to increase the duration of the measuring process, there are provided the following additional elements: a delay circuit or line for delaying in time the signal, a generator of impulses randomly distributed in time; a sixth AND gate whose one input is connected to the input terminal (source of input pulses) and whose second input is connected to the random generator; the input terminal is directly connected with S-input of the first RS flip-flop. The output of the sixth AND gate is connected with the inlet of the counter of input impulses and with the first input of the first AND gate. The time delay circuit is connected between the output of the first AND gate and the R input of the first RS-flip-flop. The output of the first AND gate is also connected to the input of the counting trigger, between the input of the counting trigger FF and R input of RS flip-flop.

3. In a different modification, the analyzer of impulse processes of heart activity for the purpose of determination of values of measured parameters as a function of time, the source of input pulses is connected with the first input of the first AND gate; the outlet of the second AND gate is directly connected with the input of the binary counter of imput impulses provided with r outputs; the inlet of the first reading counter of impulses provided with a digital count indicator is connected with the output of the first AND gate.

4. In still another modification for the purpose of eliminating influence of accidental disturbances on the results of the measurements, there are used mutually independent sources or detectors of input impulses to be evaluated. For instance two detectors of pulse beats are provided of which one dectector is arranged on the right hand of a patient and the other detectors is arranged on the left hand thereof; the inlet of the first detector is connected directly with one input of an AND gate whereas the output of the second detector is connected with the second input of the AND gate, via a regulated time delaying circuit; the output of the AND gate is connected with the input terminal of one of the previously described devices.

The novel features which are considered as characteristic for the present invention are set forth in particular in the appended claims. The invention itself, however, will be best understood from the following description of preferred embodiments which is accompanied by the following drawing.

DESCRIPTION OF PREFERRED EMBODIMENTS

Figure 1:
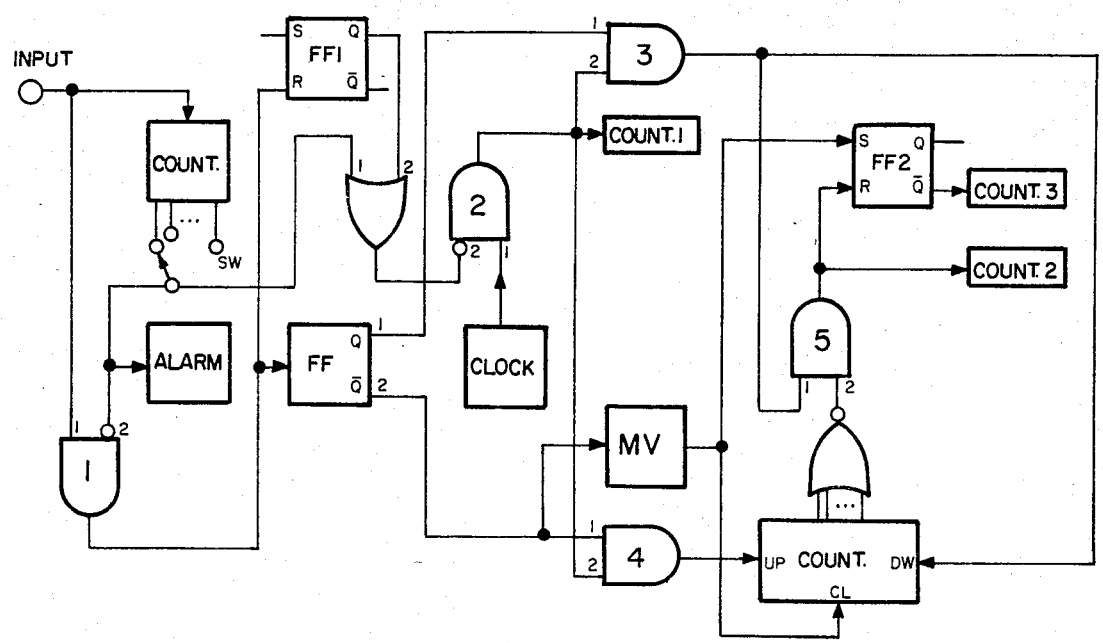
FIG. 1 is a block diagram of an embodiment of the device of this invention for determining value of measured parameters as a function of a given number of impulses $N_m = 10^{m+l}+1$, where $m = 1,2 \ldots$, which gives the possibility to express the measured values as a percentage of analyzed number of time intervals $10^{m+1}$. To express the obtained results in percents it is necessary to divide the counted value by $10^{m+1}$.
Figure 2:
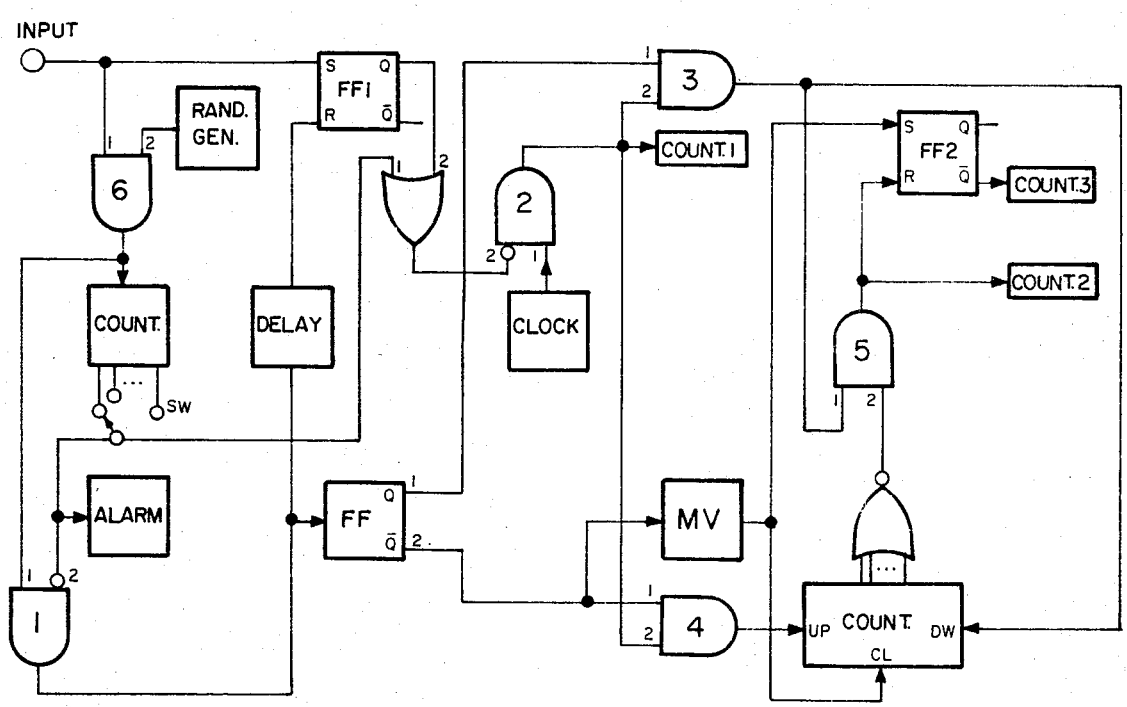
FIG. 2 is a block diagram of another embodiment of the device of the invention for determining the values of measured time intervals in a selected sample or set of time intervals. For reading in percents the amount is a multiple of $10^{m-1}$.
Figure 5:
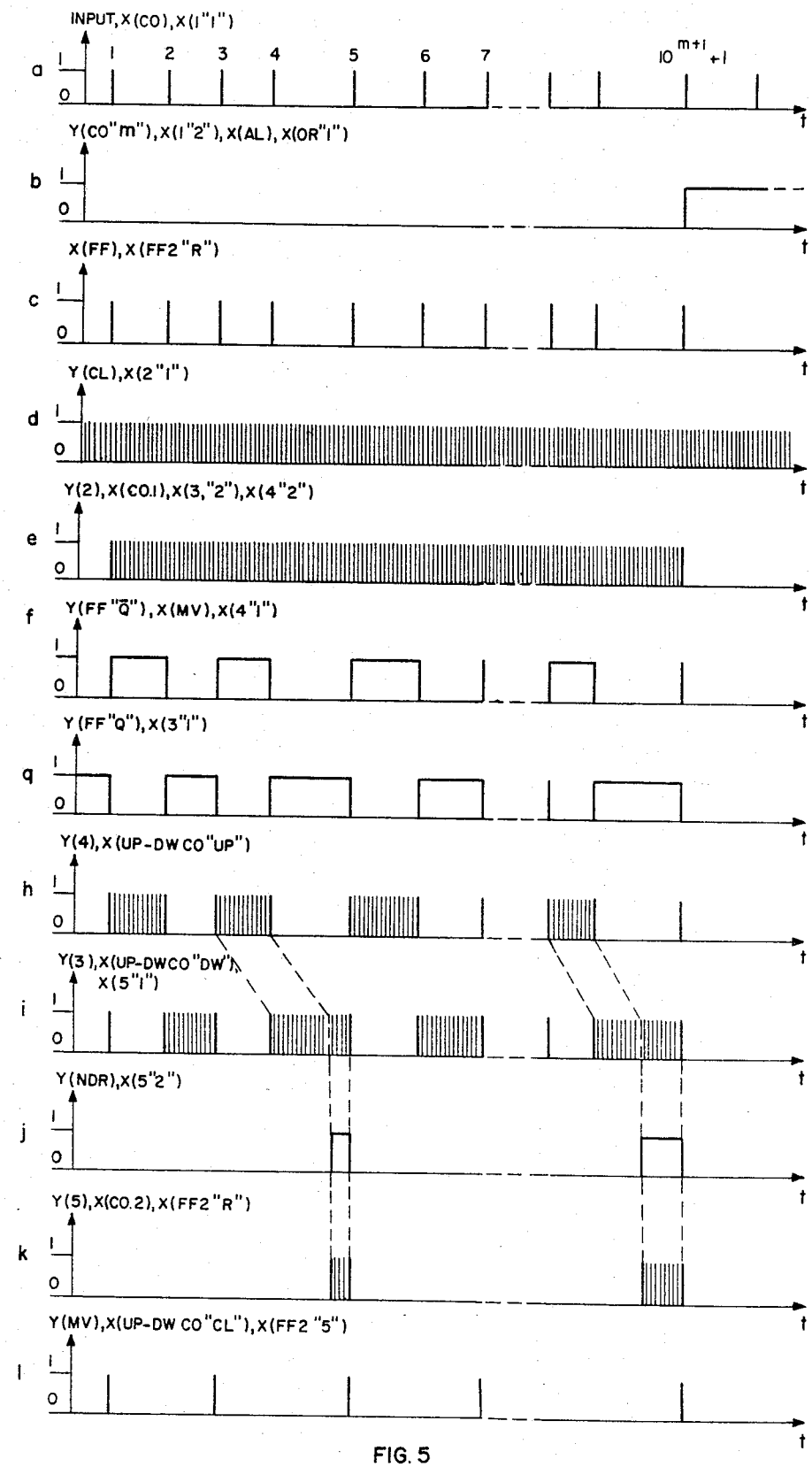
FIG. 5 is a time diagram of operation of the device of FIG. 1.
Figure 6:
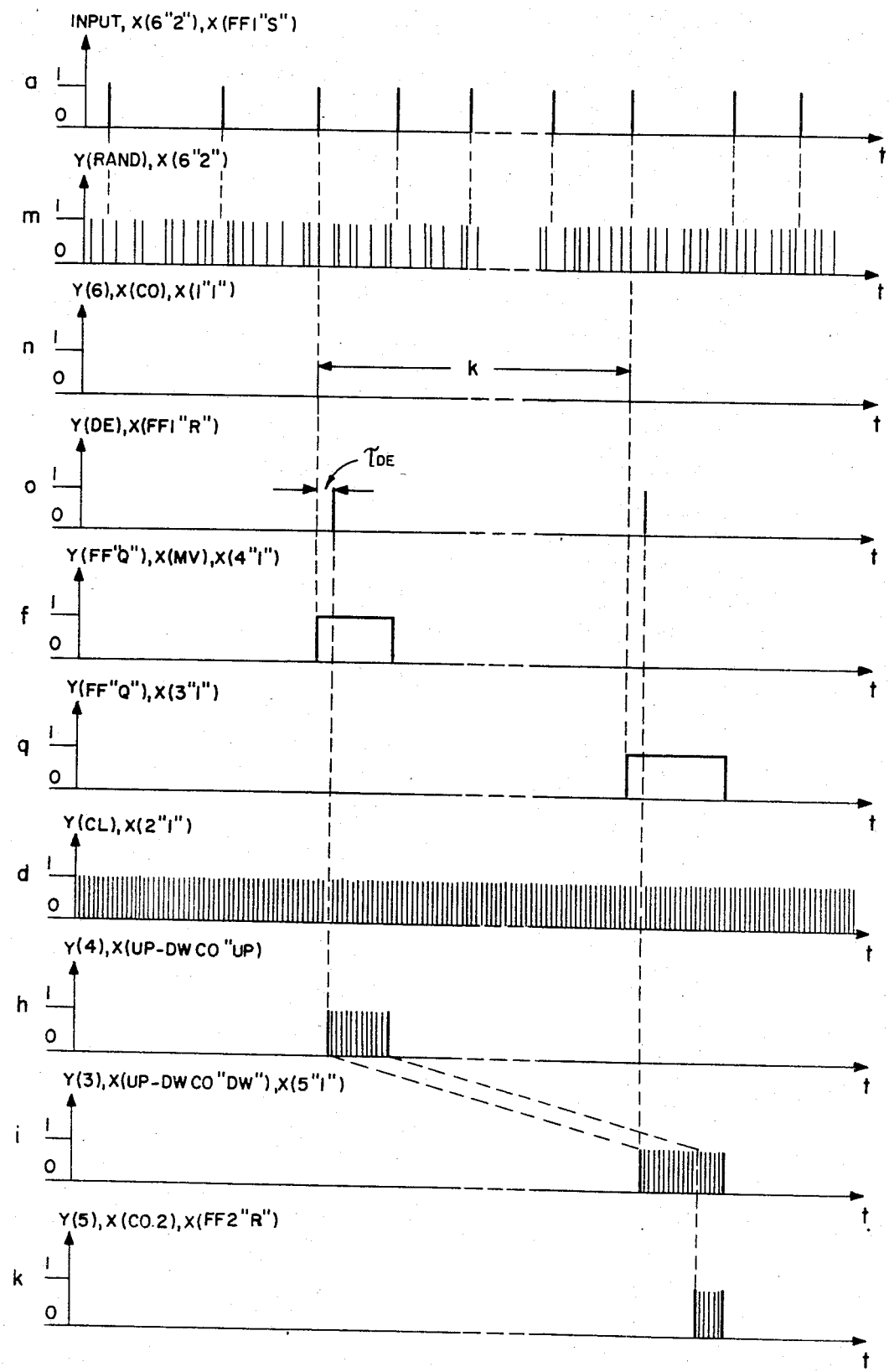
FIG. 6 is a time diagram of operation of the device of FIG. 2.

Referring firstly to FIGS. 5 and 6, reference character X denotes inputs and Y denotes outputs of the block circuits and logic elements in corresponding FIGS. 1 and 2. In FIGS. 5 and 6 the first subscript in parentheses identifies the name or the reference character of the block and/or logic element, the second subscript in parentheses identifies the input or output; for example X (2 "A") means the first input of the second AND gate, Y (FF 2 "Q") means the Q output of the second flip-flop FF2. For the blocks and logic elements having only one input or only one output, only inlet X or only outlet Y is added to the reference character of the block, for example X (MV) or Y (MV).

The operation of the analyzer of processes of heart activity according to FIG. 1 will be explained with reference to FIG. 5. In the time diagram a) of FIG. 5 there is illustrated a sequence 1 to $10^{m+1}$ of the analyzed impulses received at the input terminal of the device. Before the actuation of the device, all counters of impulses. Namely the input counter, counter 1, counter 2 and counter 3, and the up-down counter UP-DW, are cleared, so that the readings of all these counters are set to zero. If the measurements are to be carried out in the m-th range then with the aid of the multiposition switch SW the reading of the corresponding count of impulses is obtained from the m-th output $(M = 1,2 \ldots R)$ Y(CO "m"). The reading at the m-th output of the input counter of impulses Y(CO "m") or at the R-position switch SW Y(SW) is determined in accordance with the following equation:

$$Y(CO \text{ "}m\text{"}) = \begin{cases} 0, \text{ if } N < 10^{m+1} + 1 \\ 1, \text{ if } N \geq 10^{m+1} + 1, \end{cases}$$

wherein N is the number of impulses supplied from the beginning of measurements to the input X (CO) of the input counter, see diagram b) in FIG. 5. The first RS flip-flop FF1 and the trigger FF with the single counting inlet are assymetrical and at the initial period of measurements within the interval between the time point of starting the device and of the supply of a first impulse to its input terminal, the circuits FF and FF1 are placed to a position in which their Q outputs are at logic 1. Hence before the number $N < 10^{m+1} + 1$ of input pulses is applied to the input terminal of the device and therefore to the input of the binary counter of impulses, X (CO), the inversed second input of the first AND gate 1. i.e. X (1,"2"), the inlet X (AL) of the signalling device ALARM and the first input X (OR "1") of the OR gate are at logic 0 position, and to the inlet of the second trigger FF X(FF) the sequence of input impulses from the first one at the beginning of measurements to the $10^{m+1} + 1$ impulse are supplied, see diagram c) FIG. 5.

FIG. 5d shows a time diagram of the sequence of input impulses at the output Y (CK) of the clock generator. After the supply of the first impulse to the input terminal of the device, the trigger FF and the RS flip-flop FF1 change states and the output Y (OR) of the OR gate and the inverted second input X (2,"2") of the second AND gate 2 are transferred to logic 0. As a result, the impulses from the output Y(CK) of the clock generator are supplied to the input X (CO1) of the first counter 1 of impulses provided with the digital count indicator, to the second input X (3 "2") of the third AND gate 3, and to the input X (4 "2") of the fourth AND gate 4 see diagram e) in FIG. 5. Due to the supply of the first (odd) input impulse counted from the beginning of the measurements, to the input X (FF) of the trigger circuit FF, the output Y (FF "Q") of the latter is change to logic 1, see diagram f) in FIG. 5; the output Y (FF"Q") is changed to logic 0, see diagram g) in FIG. 5.

Between the odd impulses i and i+2 of the input sequence which follow one another and wherein i=1,3,5 etc, there are i-th odd and i+1 even time intervals corresponding to the time intervals $\tau_i$ and $\tau_{i+1}$ between the impulses of the analyzed sequence. At the occurance of each odd impulse of the input sequence, the output Y (FF"Q") of the counting trigger FF, the first input X (4 "A") of the fourth AND gate 4 and the input X (MV) of the multivibrator MV are changed to logic 1.

A short time impulse (see diagram 1) in FIG. 5) appears at the outlet Y (MV) of the multivibrator MV, and this short impulse is supplied to the clearing input of the UP-DOWN counter of impulses UP-DW and to the S input of the second flip-flop FF2. The clearing impulses are supplied from the output of the multivibrator MV immediately after the supply of each odd impulse, as a result of this there are nulified the readings at the output of the UP-DOWN counter of impulses and the $\overline{Q}$ output of the second flip-flop FF2 is set to 0. Among the impulses at the output of the multivibrator MV there are included two intervals of time between the impulses of the input sequences: namely the odd i-th and the even i+1 interval. The i-th and the i+1-th time intervals between the inlet impulses arranged between two successive clearing impulses at the output of the multivobrator MV, form an i-th comparison pair of the various time intervals $(\tau_i, \tau_{i+1})$. After the supply of the first impulse pulse counted from the beginning of actuation, to the input terminal of the device, the tact or clock impulses are supplied to the input X (CO1) of the first reading counter 1 of the impulses with digital count indicator and to the DW input of the UP-DOWN counter, whereby during the odd time intervals the clock impulses are supplied to the summarizing or upward counting input X (UP) of the latter, see diagram h) in FIG. 5. During the even time intervals they are supplied to the subtracting or downward counting input X (DW) and to the first input X (5"1") of the fifth AND gate 5, see diagram i in FIG. 5.

Since from the beginning of each odd interval of time $\tau_i$ the impulse from the output Y (MV) of the multivibrator MV supplied to the clearing input X (CL) of the UP-DOWN counter of impulses nulifies the reading of the latter counter of impulses therefore during all these odd intervals of time $\tau$ after supply to its inlet of the first tact impulse in this interval, the readings at the output Y (CO "UP-DW") of the Up-DOWN counter will be different from 0; therefore the output Y (NOR) of the NOR gate will be equal to 0. This reading will not change during the next even time interval $\tau_{i+1}$ until the number of the obtained tact or clock impulses during the increase of the even time intervals will remain less than the number of impulses $n_i$ supplied to the upward counting input of the UP-DOWN counter of impulses during the whole receding of time interval $\tau_i$. If after the end of the odd time interval the number of clock pulses $n_{i+1}$ is less than the number $n_i$, then the output Y (5'2) of the fifth AND gate 5 will remain in the 0 condition and in this phase of comparison including the odd $\tau_{i+2}$ and the subsequent even $\tau_{i+3}$ time intervals between the impulses of the input sequence, the readings of the counters 2 and 3 provided with digital count indicators will not change.

Before the start of the next cycle of comparison including the odd $\tau_{i+2}$ and even $\tau_{i+3}$ time intervals between the input impulses, the remaining reading $n_i-n_{i+1}$ on the UP-DOWN counter will be cleared by the impulse supplied from the output of the multivibrator MV to the CL input of the UP-DOWN counter of impulses. Assuming that in i-th cycle of comparison an even time interval $\tau_{i+1}$ during which $n_{i+1}$ tact or clock impulses are generated, is greater than the odd time interval $\tau_i$ during which $n_i < n_{i+1}$ impulses are generated. In this case, after the supply to the input X (DW) of $n_i$ tact or clock impulses during the even time interval $\tau_{i+1}$ of this cycle of comparison of the values of time intervals, the readings at the outputs of all ranges or orders of the UP-DOWN counter of impulses will be equal to 0 and as a result of this the reading at the output Y (NOR) of the NOR gate and at the second input X (5"2") of the fifth AND gate 5 will be equal to 1. see diagram J) in FIG. 5. The first input X (5"1") of the fifth AND gate 5 during this cycle of comparison will be supplied additionally with $n_{i+1}-n_1$ tact or clock impulses which will be counted at the second reading counter 2 with the digital indicator, see diagram k) in FIG. 5.

In this cycle of comparison at least one impulse is applied to the output Y (5) of the fifth AND gate 5 and therefore to the R input of the second flip-flop FF2. The latter flip-flop will change its state and its Q output will be at logic 1 and the readings of the third reading counter 3 of impulses provided with the digital count indicator will increase by one, regardless of the number of impulses (more than one) supplied to the input X (FF 2"R") during this cycle. In this manner the readings of the second reading counter 2 provided with the digital count indicator, during the i-th cycle of comparison increases to a number $A_i$ wherein $$A_i = \frac{n_{i+1} - n_i + |n_{i+1} - n_i|}{2}$$

At the end of the measuring session the measurement including $10^{m+1}/2$ cycles of comparison of the values of paired intervals $\tau_i$, $\tau_{i+1}$, the readings of the second reading counter 2 provided with the digital indicator will be equal $$A = \sum_{i=1}^{10^{m+1}/2} A_i$$

and the readings of the third reading counter 3 provided with the digital count indicator during the i-th cycle of comparison will increase by one if in this cycle of comparison $A_i<1$.

After the input terminal of the device is supplied with $10^{m+1}+1$ impulses of the analyzed sequence or with $10^{m+1}$ of time intervals between the impulses, the m-th output Y (COUNT "m") of the counter of input impulses, the inversed second input X (A "2") of the first AND gate 1, the input X (AL) of the signaling device ALARM and the first input X (OR "1") of the OR gate 1 will change their states to logic 1, see diagram b. FIG. 5. As a result of this the signalling device ALARM is actuated, the supply of the input impulses to the input X (FF) of the counting flip-flop FF will be interrupted, the supply of the clock impulses to the second input X(3 "3") and X (4"2") of the third and fourth AND gates and to the input X (CO 1) of the first reading counter 1 provided with the digital counter indicator is also interrupted. Thus, the first counter of impulses 1 with the digital count indicator will show the total time $T_m$ of $10^{m+1}$ successive time intervals between impulses of the input sequence $$T_m = \sum_{j=1}^{10^{m+1}} \tau_j \, (j = 1, 2 \ldots)$$

The average time interval between two input impulses will be expressed as follows:

$$\tau_E = \frac{T_m}{10^{m+1}}$$

For example, if $m=1$, then $\tau_E = T_m/100$; for $m=2$ $\tau_E = T_m/1000$. Correspondingly, the average frequency of the impulses of the input flow $F_e$ will be equal $F_e = 1/\tau_E$. 60 impulses/min.

The second reading counter 2 with the digital count indicator will show the sum of the values of the positive excess of the number of tact or clock impulses during the even time intervals $\tau_{i+1}$ relative to the number of tact impulses in in the odd time interval $\tau_i$ in each cycle of the comparison contained between two clearing impulses Y (MV)

$$A = \sum_{i=1}^{d} A_i, \text{ wherein } d = \frac{10^{m+1}}{2}$$

The third reading counter 3 of impulses provided with the digital count indicator shows the number $N_a$ of the cycles during the time of measurement during which the even time intervals exceeded in value the preceding odd time intervals or the number of arrhythmia cycles of comparison $$N_a = \sum_{i=1}^{10^{m+1}} f(\tau_{i+1} - \tau_i)$$

wherein $$f(\tau_{i+1} - \tau_i) = \begin{cases} 0, & \text{if } \tau_{i+1} \leq \tau_i \\ 1, & \text{if } \tau_{i+1} > \tau_i \end{cases}$$

The value $T_m/N_a$ is the average value of arrhythmia in seconds if $T_m$ is expressed in seconds.

Therefore the device makes possible to determine:

1. The average interval between the input impulses $\tau_E$ and therefore the average quantity $F_E$ of the impulses of the input flow determined on the base of measurements of $10^m$ time intervals between the input impulses.

2. The total value of arrhythmia A wherein the value of arrhythmia $A_i$ is absolute value of the difference between two successive time intervals between the impulses of the analyzed sequence if input pulses $$A_i = \tau_{i+1} - \tau_i$$

For the purpose of simplification of its construction the device of this invention measures and summarizes the value of arrhythmia for the i cycles of comparison starting from the odd time interval between the input impulses. In addition to this there are considered only 0.5 accidents of arrhythmia when in the cycle of comparison the even time interval $\tau_{i+}$ exceeds in value the preceding odd time interval $\tau_i$. Therefore during the analysis of $10^{m+1}$ of the time intervals between the input impulses of the sequence the value of arrythmia in $10^{m+1}/4$ cycles of comparison is determined of which each is composed of two successive time intervals between the time moments of supply of the inlet impulses.

3. The number of occurances or cases of the presence of arrhythmia $N_a$ in $10^{m+1}/4$ comparisons between two successive time intervals. The presence of arrhythmia is the case when $\tau_j \neq \tau_{j+1}$. If $m=1$, than 4 $N_a$ shows the percentage of the cases of arrhythmia; if $m=2$ than $0.4 N_a$ is the percentage of the accidents of arrhythmia etc. In general, the percentage of arrhythmia $$L = \frac{4 N_a}{10^m - 1}$$

4. The average value of arrhythmia or the average absolute value of the difference between the successive unequal time intervals among the impulses of the input flow $$A_E = \frac{A}{N_a}$$

The operation of the analyzer of the impulse processes of heart activity in accordance with the embodiment of FIGS. 2 and 6 is as follows:

For the purpose of elimination of the possible influence of the periodicity of the analyzed processes upon the results of the measurements and for the purpose of increasing the duration of the exposure (session of measurements) with the unchanged number of ranges or orders used in the counters of impulses, the cycles of comparison are formed from the time intervals $\tau_p$ and $\tau_{p+1}$ between the inpulses of the measured input sequence obtained by random selection of these time intervals between the impulses of the input sequence.

The time intervals $\tau_p$ and $\tau_{p+1}$ which form the cycle of comparison wherein $p=1,3,5$ is the numbering of the time intervals in the total amounts random selection, and between the time intervals $\tau_p$ and $\tau_{p+1}$ there can be arranged a random number K of time intervals of the $\tau_j$ of the total amount of intervals, wherein $k=1, 2 \ldots$.

With the aid of the generator RAND GEN of randomly in time distributed impulses and the sixth AND gate 6, from the total amount of impulses (see diagram a, FIG. 6) of the analyzed pulse sequence and from the randomly in time distributed impulses from the generator RAND GEN (see diagram m, FIG. 6) there is selected a random sequence of impulses (see diagram n. FIG. 6) from the output Y (6) of the sixth AND gate 6. The randomly selected impulses from the output of the sixth AND gate 6, similarly to the device in accordance with FIG 1, are supplied to the first input X (1 "1") of the first AND gate 1 and to the counter COUNT having R outputs. The first impulse of the input sequence which coincides with the inpulses of the random impulse flow supplied from the generator RAND GEN, as well as the first input impulse in the device according to FIG. 1, will change the state of the counting trigger FF and the first RS flip-flop FF1. The impulse applied to the reset input X (FFI "R") of the first RS flip-flop is supplied with a certain time delay $\tau_{p1}$ relative to the signal supplied to the input of the counting trigger FF. The value $\tau_{d1}$ is determined by the parameters of the delay line DELAY (see diagram o, FIG. 6). Similarly to the device of FIG. 1,5 the tact or clock impulses will start to be supplied to the following points: the input X(CO"1") of the first reading counter 1 of impulses with the digital indicator, the input X (MV) of the multivibrator MV. and the upward input of the UP-DOWN counter of impulses. The whole process, as explained above in the device according to FIG. 1, will be repeated as shown in the time diagrams f,d,h,i,k in FIGS. 5 and 6.

In contrast to the device in accordance with FIG. 1, the supply of the z+1 impulse of the input flow of impulses will lead to the return of the first RS flip-flop FF1 to the original position in which the output Q of the latter is at logic 1 and the supply of impulses of the CLOCK generator from the output of the second AND gate 2 is terminated until the appearance of the second randomly coincided impulse which is the z+k-th impulse of the inpulse pulse sequence, wherein z is a serial number of the first impulse of the input sequence from the beginning of measurements which randomly coincided in time with an impulse from the generator RAND GEN of the randomly distributed impulses. After the time interval $\tau_{de}$ and after the second randomly coincided impulse of two impulse sequences, the output Q of the first RS flip-flop circuit will change its state to logic 0 and the clock impulses will start to be supplied to the input of the first reading counter 1 of impulses and to the subtracting or downward input DW of the UP-DOWN counter of impulses. Thereby, the analyzed time interval starts by a z-th input impulse and ends by the z+1-th impulse, and the cycle of comparison consists of z and z+k time intervals between the input impulses. The cycles can contain both similar and dissimilar by evenness time intervals between the impulses of the input time sequence. The cycles similar to those in the device according to FIG. 1 contain an odd and a following even time interval of the random total number. K>1 is a random natural number.

The value of the time interval $\tau_e$ of the delay in signals carried out by the DELAY circuit is small and its influence can be neglected since all time intervals of the selected sample are shortened by constant value $\tau_{de}$. The average value of the number K or the coefficient of the read count of impulses can be changed by respective selection or setting of the duration $\tau_{in}$ of impulses of the input sequence and of inpulses of the randomly distributed in time pulse sequence $\tau_{RAND}$.

By selection of $\tau_{in}$ and $\tau_{RAND}$ it is possible to regulate the coefficient of any count and thereby to set the approximate duration of the performed measurements.

Figure 3:
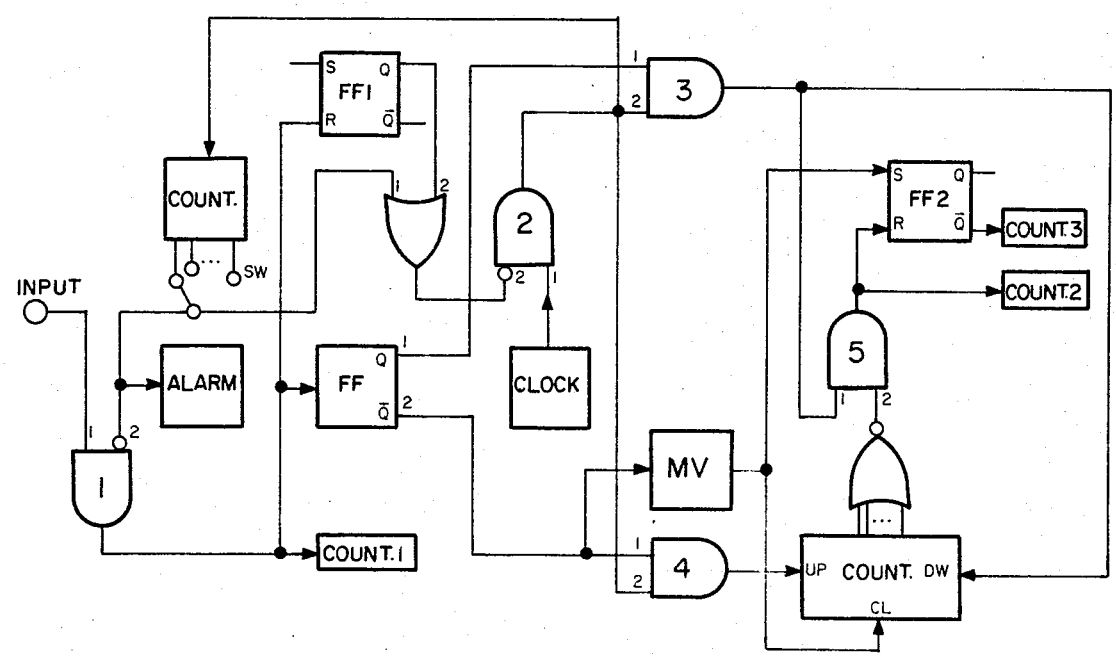
FIG. 3 is a block diagram of still another embodiment of the device of the invention for measuring values of parameters as a function of time.

The operation of the analyzer of impulse processes of heart activity in accordance with FIG. 3 is as follows:

One of the characteristics of the discrete processes is the frequency of impulses, for example at the present time it is accepted to characterize of the condition of patient's pulse by the frequency of beats expressed in the number of beats or impulses per minute (Imp/min). In the analysis of the impulse processes of the heart activity in accordance with the device of FIG. 3 the measurements are carried out in accordance with given time of exposition T, but not in accordance with the given number of input impulses N as is the case in the analysis of impulse processes according to FIGS. 1 and 2. The inlet of the counter of impulses COUNT is connected with the output Y (2) of the second AND gate 2. After the supply of the first input impulse of the analyzed sequence to the input terminal of the device to the input X (CO) of the binary counter of impulses, clock impulses will start to be supplied. The first output Y (CO"1") of the counter of impulses COUNT is changed to logic 1 if the number of clock impulses $M_1$ supplied to its input X (CO) is determined in accordance with the condition $$M_1 = \frac{60}{\tau_{cl}}$$

wherein $\tau_{cl}$ is time interval between tact or clock impulses. In general $$M_m = \frac{60 \cdot 10^{m-1}}{\tau_{cl}}.$$

Figure 4:
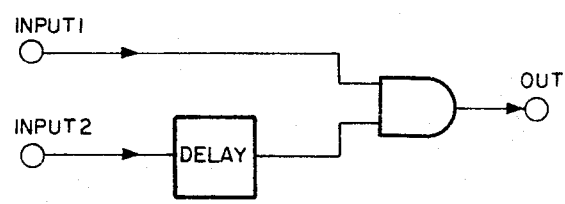
FIG. 4 is a block diagram of a modified source of inlet pulses provided for reducing the influence of accidental disturbances during the process of detecting impulses in the analyzed sequence.

The operation of the inlet circuit for the analyzer of impulse processes of heart activity in accordance with FIG. 4 is as follows:

Several accidental factors which lead to the appearance of disturbances such as false impulses, act upon the detectors of impulse processes, for example on a sensor which converts the pulse beats into electrical signals. For the purpose of reduction of the influence of the random disturbances, for example during registration of impulses of heart beat wherein the sensor which registers the impulses of filling with blood of the capillaries in a thumb finger, the composite input to the analyser of impulse processes includes sensors where one sensor is used for the right hand, the other for the left hand with the regulated line of signal delay connected to the sensor for the left hand. The formed impulses from both sensors are supplied to the respective inputs of an AND gate. With the aid of the regulated line of signal delay, the inpulses supplied from the left and right sensors of impulses are coincident in time and the reading are taken from the outlet of AND element which is connected with the inlet input of the devices - analyzers of impulse processes in accordance with FIGS. 1, 2 and 3.

If the probability of the appearance of the false impulse in one of the sensors is equal to P, then the probability of the appearance of the conicided in time false signal will be equal to $P^2$, for example if the probability of the appearance of the false signal in one sensor is equal 0.01 then the probability of the coincided in time false signal will be equal 0.0001.

This increases the quality of the obtained results of measurements of the time parameters of the analyzed impulse flow. It is also possible to use more than 2 sensors, for example 3 and correspondingly two logic elements AND or two delay lines DELAY. The analyzer of the impulse processes of heart activity in accordance with FIGS. 1, 2 and 3 can be designed as a simple device with a method of measurements in accordance with each of these figures, and using a switch to select a desired kind of measurements. For example, for transition from the measurements in accordance with the mode of operation of FIG. 2 to the mode of measurements in accordance with FIG. 1 it is sufficient to short circuit the input X (6"1") and the output Y (6) of the sixth AND gate 6, to disconnect inputs of the first flip-flop RS from the input terminal of the device and to connect directly the inlet with the outlet of the delay circuit, if necessary. The comparison of the results of measurements in accordance with FIG. 1 (determinated) and FIG. 2 (random) can characterize the periodicity of the rhythmical phenomena in the analysed input flow.

The invention is not limited to the details shown since various modifications and structural changes are possible without departing in any way from the spirit of the present invention.

What is claimed and desired to be protected by Letters Patent is set forth in particular in the appended claims:

1. A device for analyzing impulse processes of heart activity such as for determining an index of arrhythmia, comprising an input terminal for receiving a sequence of input pulses to be analyzed; a first AND gate having an input, an inverted input and an output; a counter having an input connected with said input terminal and a plurality of outputs; a multiposition switching means connected between respective outputs of said switching means and the inverted input of said first AND gate; signalling means connected to the inverted input of said first AND gate; a counting trigger having an input and two outputs; a first flip-flop circuit having a set and a reset input and two outputs; the output of said first AND gate being connected to the input of said counting trigger and to the reset input of said flip-flop circuit; an OR gate having an input connected to one output of said flip-flop circuit, another input connected to the inverted input of said first AND gate, and an output; a second AND gate having an inverted input connected to the output of said OR gate, another input and an output; a clock pulse generator connected to the other input of said second AND gate; a plurality of reading counters each having an input and a count display; a third AND gate, a fourth AND gate and a fifth AND gate each having two inputs and an output; an up-down counter having a plurality of inputs and outputs, one input of said third and fourth AND gates being connected to a respective one of the inputs of said up-down counter and to the output of said second AND gate; the other inputs of said third and fourth AND gates being connected to respective outputs of said counting trigger; a multivibrator having an input connected to the other input of said fourth AND gate and an output; said inputs of said UP-DOWN counter having an up counting input, a down counting input and a clearing input; a second flip-flop circuit having a set input and a reset input, the set input being connected to the output of said multivibrator and to said clearing input; a NOR gate having a plurality of inputs connected to respective outputs of said UP-DOWN counter; and an output connected to an input of the fifth AND gate, the other input of the latter gate being connected to the output of said third AND gate and to said down counting input; the output of said fifth AND gate being connected to the reset input of said second flip-flop circuit and to a second one of said reading counters; and the output of said second flip-flop circuit being connected to a third of said reading counters.

2. A device as defined in claim 1, wherein for the purpose of decreasing the influence of periodicity of the impulse processes, there are provided a sixth AND gate having two inputs and an output; a random in time pulse generator; and a delay circuit; and input of said sixth AND gate being connected to said input terminal and to the set input of said first flip-flop circuit, the other input thereof being connected to said random in time generator and the output thereof being connected to the input of said binary counter and to the input of said first AND gate; and the output of said first AND gate being connected to the reset input of said first flip-flop circuit via said delay circuit.

3. A device as defined in claim 1, wherein for the purpose of determining values of measured parameters as a function of time, the input of said counter is connected to the output of said second AND gate; said input terminal being connected to the input of said first AND gate and the output of the latter being connected to the first one of said reading counters.

4. A device as defined in claim 1, wherein for the purpose of eliminating the influence of accidental disturbances on the results of measurements, there are provided two input terminals for receiving two mutually independent pulse sequences to be analyzed, a delay circuit, an AND gate having an input connected to one input terminal, another input connected via said delay circuit to the other input terminal and an output coupled to said counter or the input of said first AND gate.

* * * * *